(12) United States Patent
Jardret et al.

(10) Patent No.: US 11,786,411 B2
(45) Date of Patent: Oct. 17, 2023

(54) MULTIPLE-WOUND NEGATIVE PRESSURE WOUND THERAPY USING MULTIPLE FLUID COLLECTION VOLUMES

(71) Applicant: DeRoyal Industries, Inc., Powell, TN (US)

(72) Inventors: Vincent Denis Jardret, Powell, TN (US); Jonathan Matthew Cayce, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 17/690,064

(22) Filed: Mar. 9, 2022

(65) Prior Publication Data

US 2022/0192887 A1    Jun. 23, 2022

Related U.S. Application Data

(62) Division of application No. 16/575,614, filed on Sep. 19, 2019, now Pat. No. 11,298,268.

(Continued)

(51) Int. Cl.
*A61F 13/00* (2006.01)
*A61F 13/02* (2006.01)

(52) U.S. Cl.
CPC .. *A61F 13/00068* (2013.01); *A61F 13/00021* (2013.01); *A61F 13/0216* (2013.01); *A61F 2013/00174* (2013.01)

(58) Field of Classification Search
CPC ............ A61F 13/00021; A61F 13/0216; A61F 2013/00174; A61F 13/00068
See application file for complete search history.

(56) References Cited

U.S. PATENT DOCUMENTS

| 5,636,643 A | 6/1997 | Argenta et al. |
| 5,830,198 A | 11/1998 | Henniges et al. |

(Continued)

FOREIGN PATENT DOCUMENTS

FR      2965182 B1    5/2013

OTHER PUBLICATIONS

Authorized Officer Lee Young, Notification of Transmittal of the International Search Report and the Written Opinion of the International Searching Authority, or the Declaration, dated Dec. 6, 2019, Alexandria, Virginia USA.

*Primary Examiner* — Susan S Su
*Assistant Examiner* — Eric Rassavong
(74) *Attorney, Agent, or Firm* — Luedeka Neely Group, P.C.

(57) ABSTRACT

A negative pressure wound therapy system treats multiple wounds on a patient's body. The system includes a source of negative air pressure, an air source, first and second fluid collection volumes, first and second wound-covering domes disposed over first and second wounds, a valve assembly disposed between the source of negative air pressure and the first and second fluid collection volumes, and between the air source and the first and second domes. The valve assembly has first and second operational modes. In the first, the valve assembly puts the source of negative air pressure in fluid communication with the first fluid collection volume, and the air source in fluid communication with the first dome. In the second, the valve assembly puts the source of negative air pressure in fluid communication with the second fluid collection volume, and the air source in fluid communication with the second dome.

6 Claims, 4 Drawing Sheets

Related U.S. Application Data

(60) Provisional application No. 62/733,131, filed on Sep. 19, 2018.

(56) References Cited

U.S. PATENT DOCUMENTS

| | | |
|---|---|---|
| 5,960,837 A | 10/1999 | Cude |
| 9,700,462 B2 | 7/2017 | DeBusk et al. |
| 2007/0009584 A1 | 1/2007 | Taheri |
| 2008/0140029 A1* | 6/2008 | Smith ................. A61M 1/94 604/313 |
| 2008/0200905 A1* | 8/2008 | Heaton ............... A61M 1/784 604/543 |
| 2010/0121287 A1* | 5/2010 | Smith ................. A61M 35/30 604/319 |
| 2010/0305524 A1 | 12/2010 | Vess et al. |
| 2011/0038741 A1 | 2/2011 | Lissner et al. |
| 2012/0053541 A1* | 3/2012 | Yao ..................... A61M 1/79 604/319 |
| 2012/0053543 A1 | 3/2012 | Miau et al. |
| 2012/0302979 A1* | 11/2012 | Locke ................. A61M 1/85 604/319 |
| 2013/0144227 A1 | 6/2013 | Locke et al. |
| 2014/0074053 A1* | 3/2014 | Locke .............. A61F 13/00068 156/60 |
| 2016/0199550 A1* | 7/2016 | Seddon ........... A61F 13/00068 604/319 |
| 2016/0256614 A1 | 9/2016 | Hall et al. |
| 2017/0224891 A1 | 8/2017 | Locke et al. |
| 2018/0177926 A1 | 6/2018 | Vernon-Harcourt et al. |
| 2019/0030224 A1* | 1/2019 | Lin ................. A61F 13/00068 |
| 2019/0201595 A1 | 7/2019 | Jardret et al. |
| 2019/0321232 A1 | 10/2019 | Jardret et al. |

\* cited by examiner

MULTIPLE-WOUND NEGATIVE PRESSURE WOUND THERAPY USING MULTIPLE FLUID COLLECTION VOLUMES

RELATED APPLICATIONS

This application claims priority to co-pending nonprovisional patent application Ser. No. 16/575,614, filed Sep. 19, 2019, titled "Multiple-Wound Negative Pressure Wound Therapy Using Multiple Fluid Collection Volumes," incorporated herein by reference in its entirety, which claimed priority to provisional patent application Ser. No. 62/733,131 filed Sep. 19, 2018, titled "Multiple-Wound Negative Pressure Wound Therapy Using Multiple Fluid Collection Canisters."

FIELD

This invention relates to the field of medical treatment of wounds by application of negative pressure to a wound site. More particularly, this invention relates to a system for medically treating multiple wounds using a negative pressure wound therapy system having multiple fluid collection canisters.

BACKGROUND

The purpose of negative pressure wound therapy (NPWT) is to apply a reduced (negative or partial vacuum) pressure to a wound to stimulate healing and remove excess exudate from the wound bed. It is known that the presence of an air flow through a lumen connecting a wound bed dressing to a waste canister that collects the exudate plays a significant role in moving the exudate from the dressing to the canister. In addition, it is known that a pressure measured at one end of a lumen is substantially equal to the pressure at the other end of the lumen as long as no fluid is present in the lumen and the lumen's inside-diameter-to-length ratio is not too small. Based on these observations, NPWT is commonly applied with dual-lumen tubing applied with a dome to maintain optimal exudate flow.

In a situation in which a patient has two or more wounds requiring negative pressure therapy, a common practice is to bridge the wounds to each other and provide a connection for both wounds to the NPWT system at a single location. In a bridged dressing in which there is a significant distance between the wound site and the dome or other connection between the dressing and the tubing that provides the reduced pressure, it is commonly observed that wound exudate removal is not executed in an optimal fashion. The reason for this is that the commonly used two lumens—the exudate removal lumen and the air flow and pressure sensing lumen—are brought in fluid communication at the dome and not at the wound bed.

Bridged wounds can be connected in a parallel or in series, thereby creating configurations in which all the wounds do not benefit from the exudate removal scheme and pressure monitoring. Further, configurations for bridged wounds often result in information specific to each wound being combined with information regarding the other wounds. For example, knowledge of the level and nature of exudate from each wound individually is important in understanding how the wound is responding to treatment.

Another common practice is to connect dressings for two or more wounds to the same pump via a "Y" connector. Using a "Y" connection between two or more wounds and the vacuum source creates a parallel configuration to deliver therapy to multiple wounds similar to the parallel configuration previously described for wound bridging. A benefit of the "Y" connector is that it eliminates the requirement to create a bridge dressing between wounds that could be labor intensive. However, the "Y" connector does not address limitations previously discussed for bridged dressings. Adverse events related to use of Y-connectors, such as disruption of therapy to at least one wound, have been noted in the FDA MAUDE database.

What is needed is a NPWT treatment configuration that enables individual monitoring of each wound, and that ensures optimal management of exudate from each wound.

SUMMARY

The above and other needs are met by a negative pressure wound therapy system for treating multiple wounds on a patient's body. In one embodiment, the system includes a source of negative air pressure, an air source, a first fluid collection volume, and a second fluid collection volume. In this embodiment, the source of negative air pressure is in fluid communication with the first fluid collection volume, the first collection volume is in fluid communication with the second fluid collection volume, and the second fluid collection volume is in fluid communication with the air source, so that the source of negative air pressure, the first fluid collection volume, the second fluid collection volume, and the air source are fluidly connected in series.

In some embodiments, the system includes a first wound-covering dome configured to be disposed over a first wound on the patient's body, and a second wound-covering dome configured to be disposed over a second wound on the patient's body. In these embodiments, the source of negative air pressure is in fluid communication with the first fluid collection volume, the first collection volume is in fluid communication with the first wound-covering dome, the first wound-covering dome is in fluid communication with the second fluid collection volume, the second fluid collection volume is in fluid communication with the second wound-covering dome, and the second wound-covering dome is in fluid communication with the air source, so that the source of negative air pressure, the first fluid collection volume, the first wound-covering dome, the second fluid collection volume, the second wound-covering dome, and the air source are fluidly connected in series.

In some embodiments, the system includes a housing that contains the source of air.

In some embodiments, the source of air comprises a vent to ambient air.

In some embodiments, the system includes a water impermeable bacterial filter in fluid communication with the vent to ambient air.

In some embodiments, the source of air comprises a source of positive air pressure.

In some embodiments, the source of negative air pressure and the air source comprise an air pump.

In some embodiments, the system includes a first canister that contains the first fluid collection volume, and a second canister that contains the second fluid collection volume.

In some embodiments, the system includes a canister that contains the first fluid collection volume and the second fluid collection volume.

In some embodiments, the system includes a water impermeable bacterial filter in fluid communication between the second fluid collection volume and the first wound-covering dome.

In another aspect, some embodiments provide a negative pressure wound therapy system that includes a source of negative air pressure, an air source, a first fluid collection volume, a second fluid collection volume, a first wound-covering dome configured to be disposed over a first wound on the patient's body, a second wound-covering dome configured to be disposed over a second wound on the patient's body, and a valve assembly. The valve assembly is disposed between the source of negative air pressure and the first and second fluid collection volumes, and between the air source and the first and second wound-covering domes. The valve assembly operates in first and second operational modes. In the first operational mode, the valve assembly puts the source of negative air pressure in fluid communication with the first fluid collection volume, and puts the air source in fluid communication with the first wound-covering dome. In the second operational mode, the valve assembly puts the source of negative air pressure in fluid communication with the second fluid collection volume, and puts the air source in fluid communication with the second wound-covering dome. Accordingly, when the valve assembly is operating in the first operational mode, the source of negative air pressure is in fluid communication with the first fluid collection volume, the first collection volume is in fluid communication with the first wound-covering dome, and the first wound-covering dome is in fluid communication with the air source, and when the valve assembly is operating in the second operational mode, the source of negative air pressure is in fluid communication with the second fluid collection volume, the second collection volume is in fluid communication with the second wound-covering dome, and the second wound-covering dome is in fluid communication with the air source.

In some embodiments, the system includes a first canister that contains the first fluid collection volume, and a second canister that contains the second fluid collection volume.

In some embodiments, the system includes a canister that contains the first fluid collection volume and the second fluid collection volume.

In another aspect, an embodiment provides a negative pressure wound therapy system that includes a source of negative air pressure, an air source, a fluid collection volume, a first wound-covering dome configured to be disposed over a first wound on the patient's body, and a second wound-covering dome configured to be disposed over a second wound on the patient's body. In this embodiment, the source of negative air pressure is in fluid communication with the fluid collection volume, the fluid collection volume is in fluid communication with the first wound-covering dome, the first wound-covering dome is in fluid communication with the second wound-covering dome, and the second wound-covering dome is in fluid communication with the air source. Accordingly, the source of negative air pressure, the fluid collection volume, the first wound-covering dome, the second wound-covering dome, and the air source are fluidly connected in series.

In some embodiments, the system includes a liquid permeable bacterial filter in fluid communication between the first wound-covering dome and the second wound-covering dome.

In yet another aspect, an embodiment provides a fluid collection canister for use in a negative pressure wound therapy system for treating multiple wounds on a patient's body. The fluid collection canister includes first and second fluid collection volumes that are separated by a wall. The first fluid collection volume has a first inlet port configured to be in fluid communication with a first wound-covering dome, and a first outlet port configured to be in fluid communication with a source of negative air pressure. The second fluid collection volume has a second inlet port configured to be in fluid communication with a second wound-covering dome, and a second outlet port configured to be in fluid communication with the source of negative air pressure.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
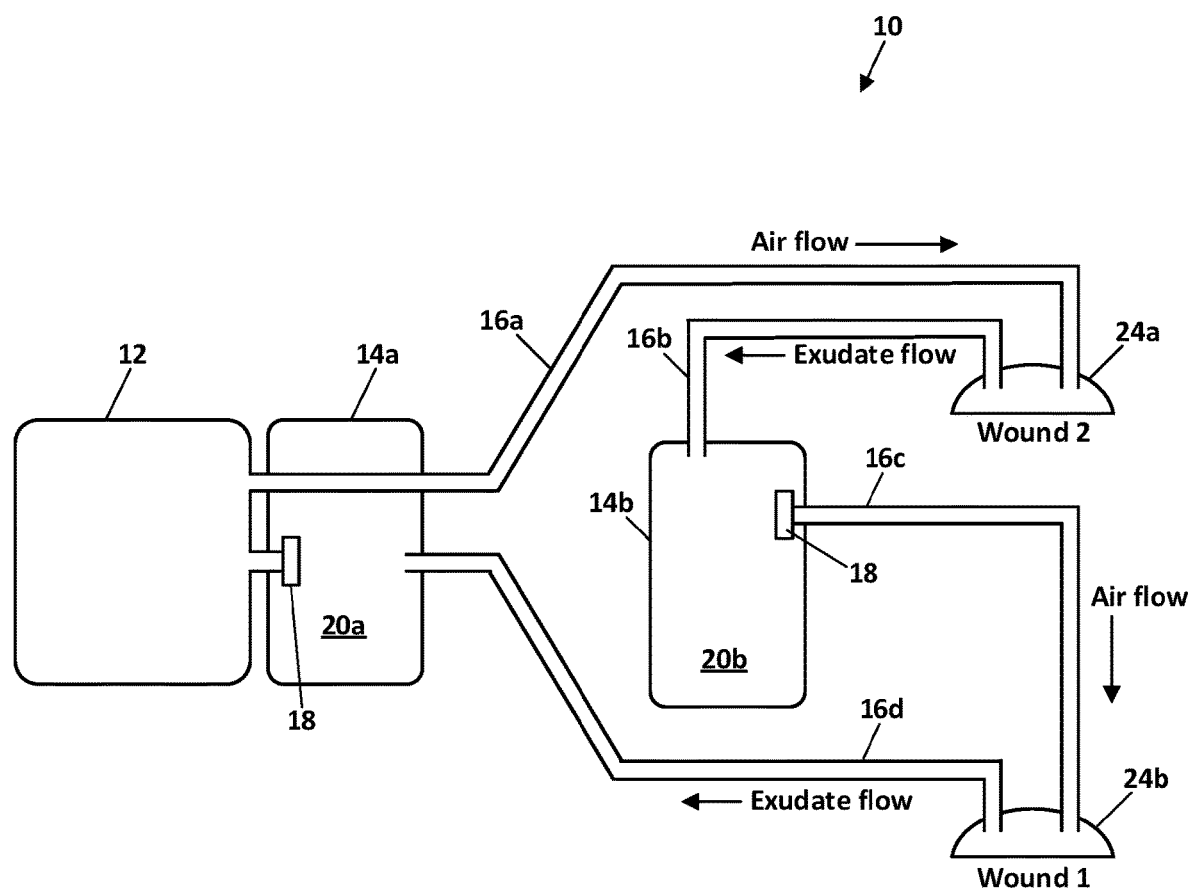
FIG. 1 depicts a dual-wound negative pressure wound therapy (NPWT) system having two canisters arranged in series according to an embodiment.

FIG. 1 depicts a first embodiment of a dual-wound NPWT system 10 in which two fluid collection canisters are connected in series. The system 10 includes a pump 12 that applies negative pressure to a volume 20a within a first fluid collection canister 14a. The negative pressure in the volume 20a is communicated through a tube 16d to the interior of a wound-covering dome 24b over a first wound on a patient's body. The negative pressure within the dome 24b is communicated through a tube 16c to a volume 20b within a second fluid collection canister 14b. An antibacterial filter 18 is provided to disinfect air moving from the volume 20b to the first wound. In a preferred embodiment, the filter 18 is water impermeable to prevent exudate mixing. The negative pressure in the volume 20b is communicated through a tube 16b to the interior of a wound-covering dome 24a over a second wound on the patient's body. A tube 16a communicates the negative pressure within the dome 24a back to the pump 12. A water impermeable antibacterial filter 18 is provided to disinfect air moving from the volume 20a to the pump 12. In the embodiment of FIG. 1, the tube 16a passes through the canister 14a, but there is no direct fluid communication between the tube 16a and the volume 20a.

Based on the application of negative pressure in the embodiment of FIG. 1, exudate from the first wound flows through the tube 16d and into the volume 20a of the canister 14a, and exudate from the second wound flows through the tube 16b and into the volume 20b of the canister 14b. Air flows from the pump 12 through the tube 16a into the dome 24a to facilitate exudate removal from second wound, and air flows from the volume 20b through the tube 16c into the dome 24b to facilitate exudate removal from first wound.

It will be appreciated that the embodiment of FIG. 1, by implementation of two exudate collection volumes, allows for wound exudate from each wound to be monitored independently (i.e., the volume, color, and consistency of the exudate.) It also enables each of the volumes to be changed out independently of the other volume. These advantages are also provided by the embodiments of FIGS. 2 and 3 discussed hereinafter.

Figure 2:
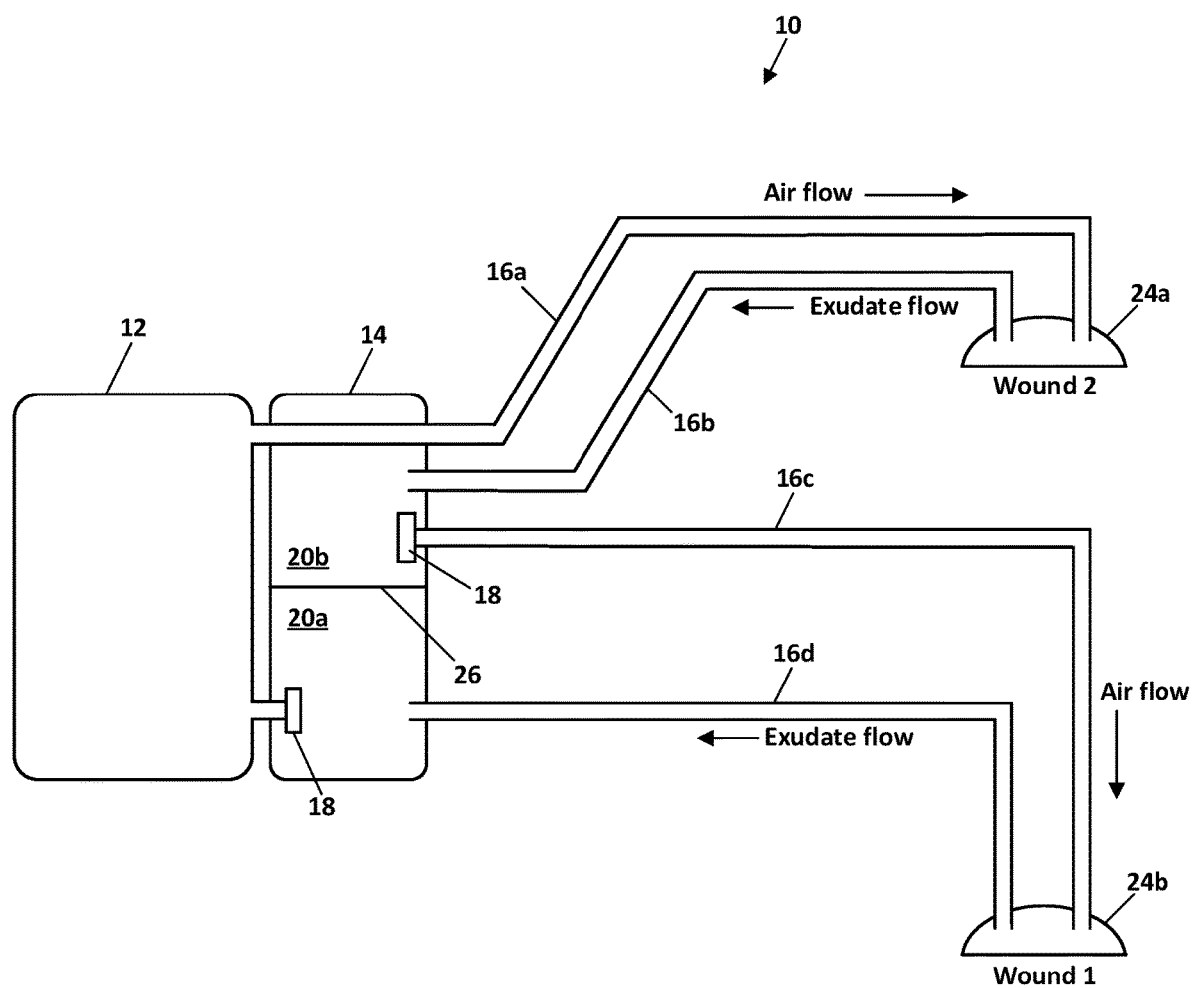
FIG. 2 depicts a dual-wound NPWT system having a single canister with two exudate collection volumes arranged in series.

FIG. 2 depicts a second embodiment of a dual-wound NPWT system 10 having a single fluid collection canister 14 containing two collection volumes 20a and 20b that are connected in series. A wall 26 in the canister 14 separates the two fluid collection volumes 20a and 20b. The system 10 includes a pump 12 that applies negative pressure to the volume 20a within a fluid collection canister 14. The negative pressure in the volume 20a is communicated through a tube 16d to the interior of a wound-covering dome 24b over a first wound on a patient's body. The negative pressure within the dome 24b is communicated through a tube 16c to the volume 20b within the fluid collection canister 14. An antibacterial filter 18 is provided to disinfect air moving from the volume 20b to the first wound. The negative pressure in the volume 20b is communicated through a tube 16b to the interior of a wound-covering dome 24a over a second wound on the patient's body. A tube 16a communicates the negative pressure within the dome 24a back to the pump 12. In the embodiment of FIG. 2, the tube 16a passes through the canister 14a, but there is no direct fluid communication between the tube 16a and either of the volumes 20a and 20b.

Based on the application of negative pressure in the embodiment of FIG. 2, exudate from the first wound flows through the tube 16d and into the volume 20a of the canister 14, and exudate from the second wound flows through the tube 16b and into the volume 20b of the canister 14. Air flows from the pump 12 through the tube 16a into the dome 24a to facilitate exudate removal from second wound, and air flows from the volume 20b through the tube 16c into the dome 24b to facilitate exudate removal from first wound.

Figure 3:
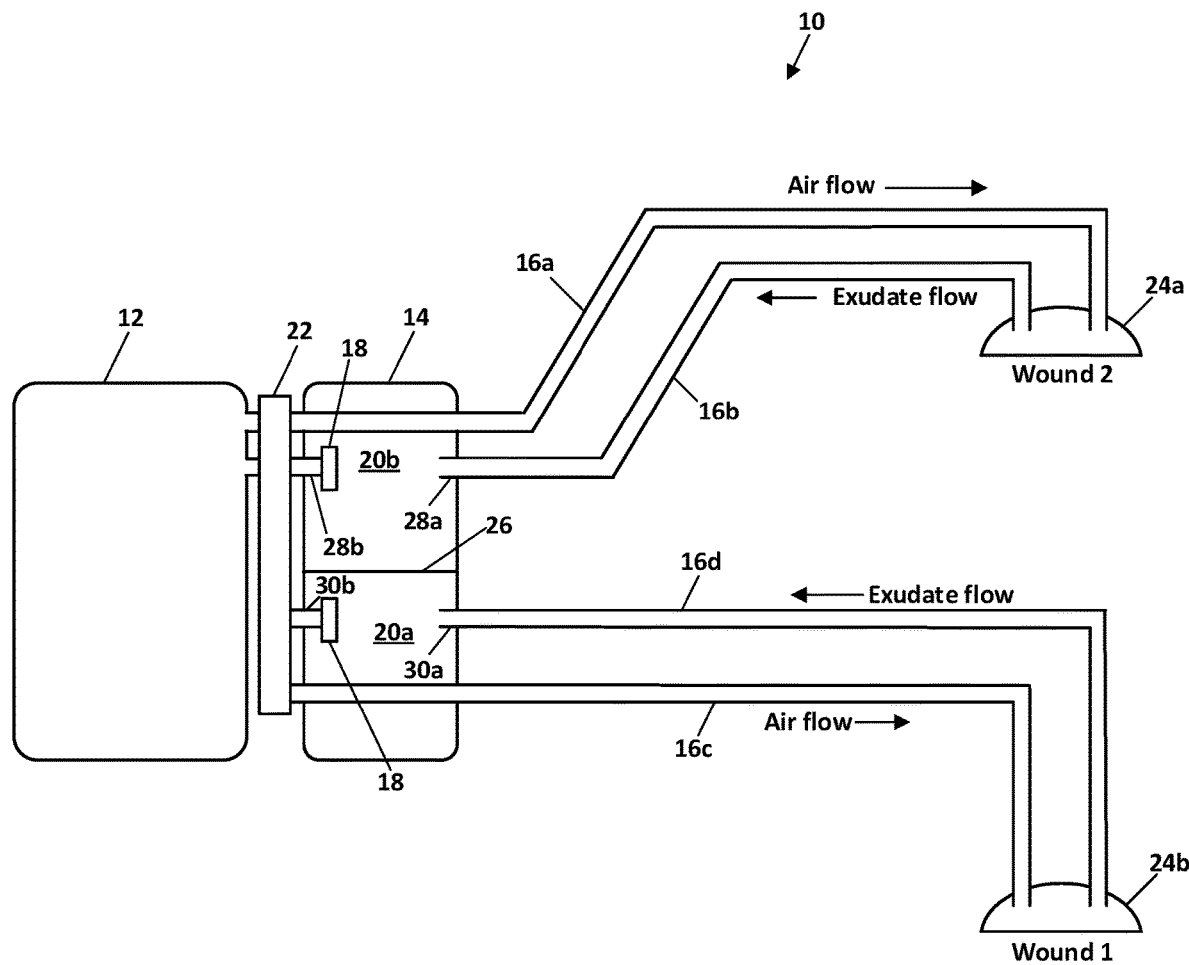
FIG. 3 depicts a dual-wound NPWT system having a single canister with two exudate collection volumes arranged in parallel.

FIG. 3 depicts a third embodiment of a dual-wound NPWT system 10 having a single fluid collection canister 14 containing two collection volumes 20a and 20b that are connected in parallel. A wall 26 in the canister 14 separates the two fluid collection volumes 20a and 20b. The system 10 includes a pump 12 that, in a first operational mode, applies negative pressure through a valve assembly 22 to the volume 20a within a fluid collection canister 14. The negative pressure in the volume 20a is communicated through a tube 16d to the interior of a wound-covering dome 24b over a first wound on a patient's body. The negative pressure within the dome 24b is communicated through a tube 16c back to the pump via the valve assembly 22. In a second operational mode, the pump 12 applies negative pressure through the valve assembly 22 to the volume 20b within a fluid collection canister 14. The negative pressure in the volume 20b is communicated through a tube 16b to the interior of a wound-covering dome 24a over a second wound on the patient's body. The negative pressure within the dome 24a is communicated through a tube 16a back to the pump via the valve assembly 22. In the embodiment of FIG. 3, the tubes 16a and 16c pass through the canister 14, but there is no direct fluid communication between the tubes 16a and 16c and either of the volumes 20a and 20b.

As shown in FIG. 3, the fluid collection canister 14 has a first inlet port 28a configured to be in fluid communication with the wound-covering dome 24a, and a second inlet port 30a configured to be in fluid communication with the wound-covering dome 24b. The fluid collection canister also has first and second outlet ports 28b and 30b configured to be in fluid communication with the valve assembly 22.

In the embodiments of FIGS. 2 and 3 discussed above, the wall 26 in the canister 14 separates the two fluid collection volumes 20a and 20b. In an alternative embodiment, the two fluid collection volumes 20a and 20b comprise two separately sealed structures that snap together or are otherwise attached together to form the canister 14. This allows each volume 20a and 20b to be changed out independently. In some embodiments, the canister 14 comprises a cage structure into which the two separate volumes 20a and 20b snap into place for use. The cage structure may be a reusable accessory, whereas the separate volumes 20a and 20b are disposed of when full.

In the embodiment of FIG. 3, the valve assembly 22 includes solenoid-actuated valves that in the first operational mode connect the volume 20a to the inlet of the pump 12 and connect the tube 16c to the outlet of the pump 12, and in the second operational mode connect the volume 20b to the inlet of the pump 12 and connect the tube 16a to the outlet of the pump 12. The solenoid-actuated valves are preferably controlled by an electronic controller that switches the positions of the valves back and forth between the first and second operational modes as necessary to maintain proper negative pressure on both wounds.

Based on the application of negative pressure in the embodiment of FIG. 3, exudate from the first wound flows through the tube 16d and into the volume 20a of the canister 14, and exudate from the second wound flows through the tube 16b and into the volume 20b of the canister 14. Air flows from the pump 12 through the tube 16a into the dome 24a to facilitate exudate removal from second wound, and air flows from the volume 20b through the tube 16c into the dome 24b to facilitate exudate removal from first wound.

Figure 4:
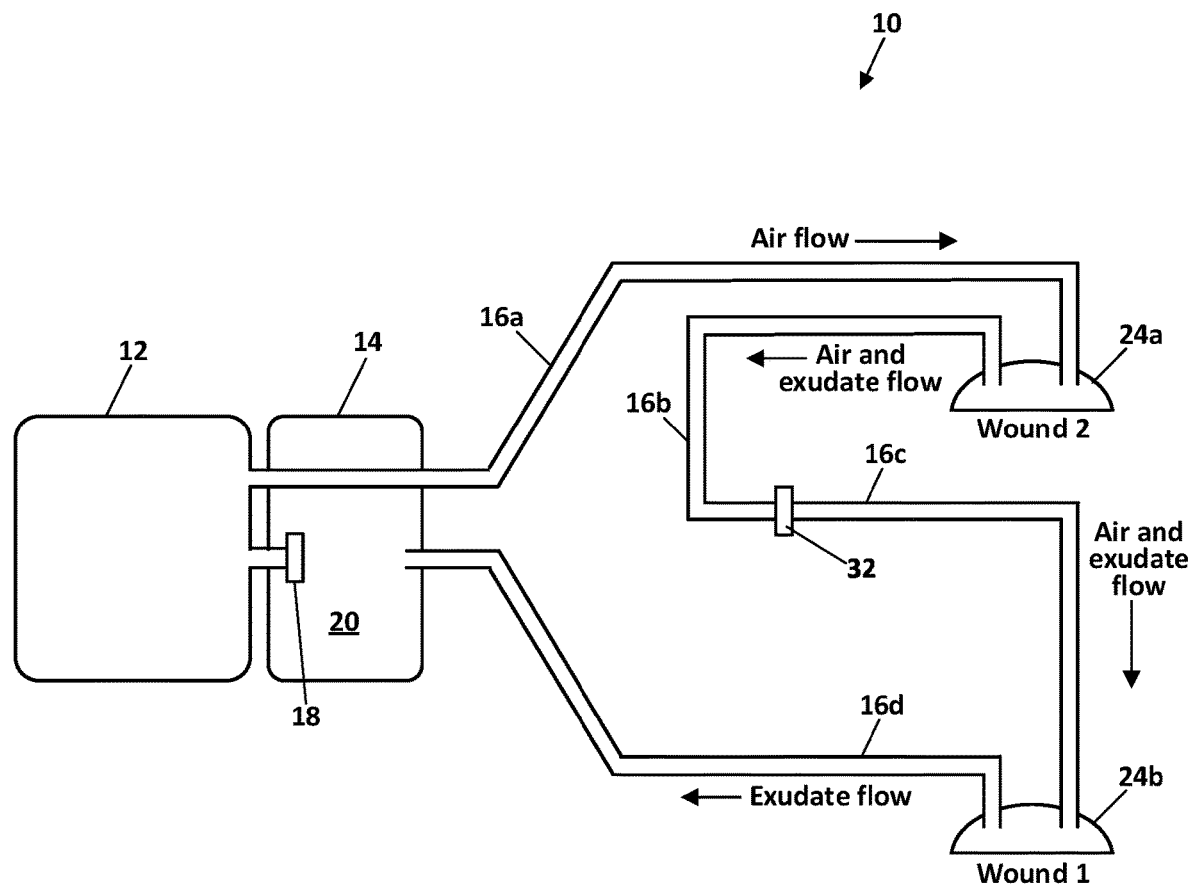
FIG. 4 depicts a dual-wound NPWT system having a single vacuum source and two wound dressings connected in series, and with a liquid permeable bacterial filter connected between the two wound dressings.

FIG. 4 depicts a fourth embodiment of a dual-wound NPWT system 10 that includes a single fluid collection canister collecting fluid from two wounds that are connected in series. The system 10 includes a pump 12 that applies negative pressure to a volume 20 within a fluid collection canister 14. The negative pressure in the volume 20 is communicated through a tube 16d to the interior of a wound-covering dome 24b over a first wound on a patient's body. The negative pressure within the dome 24b is communicated through a tube 16c and a tube 16b to the interior of a wound-covering dome 24a over a second wound on the patient's body. An antibacterial liquid permeable filter 32 is provided between the tubes 16c and 16b to disinfect the air and exudate moving from the second wound to the first wound. A tube 16a communicates the negative pressure within the dome 24a back to the pump 12. In the embodiment of FIG. 4, the tube 16a passes through the canister 14, but there is no direct fluid communication between the tube 16a and the volume 20.

Based on the application of negative pressure in the embodiment of FIG. 4, exudate from the first wound flows through the tube 16d into the volume 20 of the canister 14a. Exudate from the second wound flows through the tubes 16b and 16c, the dome 24b, and the tube 16d into the volume 20 of the canister 14. Air flows from the pump 12 through the tube 16a into the dome 24a to facilitate exudate removal from second wound, and air flows from the dome 24a through the tubes 16b and 16c into the dome 24b to facilitate exudate removal from first wound.

It will be appreciated that the embodiments of FIGS. 1, 2, and 3 may include more than two collection volumes for collecting exudate from more than two wounds. In FIG. 2 for example, the canister 14 may include multiple collection volumes like volume 20b. In the embodiment of FIG. 3, this would require additional valves in the valve assembly 22.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A negative pressure wound therapy system for treating multiple wounds on a patient's body, the system comprising:
   a source of negative air pressure;
   an air source;
   a first fluid collection volume;
   a second fluid collection volume;
   a first wound-covering dome configured to be disposed over a first wound on the patient's body;
   a second wound-covering dome configured to be disposed over a second wound on the patient's body; and
   a valve assembly disposed between the source of negative air pressure and the first and second fluid collection volumes, and disposed between the air source and the first and second wound-covering domes, the valve assembly having:
      a first operational mode in which the valve assembly puts the source of negative air pressure in fluid communication with the first fluid collection volume and not in communication with the second fluid collection volume, and puts the air source in fluid communication with the first wound-covering dome and not in communication with the second wound-covering dome; and
      a second operational mode in which the valve assembly puts the source of negative air pressure in fluid communication with the second fluid collection volume and not in communication with the first fluid collection volume, and puts the air source in fluid communication with the second wound-covering dome and not in communication with the first wound-covering dome,
   wherein, in the first operational mode of the valve assembly, the source of negative air pressure is in fluid communication with the first fluid collection volume, the first collection volume is in fluid communication with the first wound-covering dome, and the first wound-covering dome is in fluid communication with the air source, and
   wherein, in the second operational mode of the valve assembly, the source of negative air pressure is in fluid communication with the second fluid collection volume, the second collection volume is in fluid communication with the second wound-covering dome, and the second wound-covering dome is in fluid communication with the air source.

2. The negative pressure wound therapy system of claim 1 further comprising a first canister that contains the first fluid collection volume, and a second canister that contains the second fluid collection volume.

3. The negative pressure wound therapy system of claim 1 further comprising a canister that contains the first fluid collection volume and the second fluid collection volume.

4. The negative pressure wound therapy system of claim 1 further comprising a first bacterial filter in fluid communication between the first fluid collection volume and the source of negative air pressure, and a second bacterial filter in fluid communication between the second fluid collection volume and the source of negative air pressure.

5. The negative pressure wound therapy system of claim 4 wherein the first and second bacterial filters are water impermeable.

6. A negative pressure wound therapy system for treating multiple wounds on a patient's body, the system comprising:
   a source of negative air pressure;
   an air source for providing air to the multiple wounds being treated;
   a first fluid collection volume;
   a second fluid collection volume; and
   a bacterial filter for disinfecting air from the air source,
   wherein the source of negative air pressure is in fluid communication with the first fluid collection volume, the first collection volume is in fluid communication with the second fluid collection volume, and the second fluid collection volume is in fluid communication with the air source, and
   wherein the source of negative air pressure, the first fluid collection volume, the second fluid collection volume, and the air source are fluidly connected in series to move air from one of the multiple wounds being treated to another one of the multiple wounds being treated, and
   wherein the bacterial filter is fluidly connected between the first fluid collection volume and the second fluid collection volume, or between the second fluid collection volume and the air source, to disinfect the air from the air source moving from one of the multiple wounds being treated to another one of the multiple wounds being treated.

* * * * *